US008860936B2

(12) United States Patent
Sites et al.

(10) Patent No.: US 8,860,936 B2
(45) Date of Patent: Oct. 14, 2014

(54) MULTIPLE RADIATION INSPECTION OF OPHTHALMIC LENSES

(75) Inventors: Peter W. Sites, Orange Park, FL (US); Russell J. Edwards, Jacksonville, FL (US); Kenneth L. Cagle, Saint Marys, GA (US); Matt Dubin, Tucson, AZ (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 129 days.

(21) Appl. No.: 13/484,039

(22) Filed: May 30, 2012

(65) Prior Publication Data

US 2012/0327396 A1 Dec. 27, 2012

Related U.S. Application Data

(60) Provisional application No. 61/492,932, filed on Jun. 3, 2011.

(51) Int. Cl.
| | |
|---|---|
| *G01B 9/00* | (2006.01) |
| *G01M 11/02* | (2006.01) |
| *G01N 21/88* | (2006.01) |
| *G01N 21/958* | (2006.01) |

(52) U.S. Cl.
CPC ....... *G01M 11/0257* (2013.01); *G01N 21/8806* (2013.01); *G01N 2021/9583* (2013.01); *G01N 2021/8845* (2013.01)
USPC ........................................................ 356/124

(58) Field of Classification Search
None
See application file for complete search history.

(56) References Cited

U.S. PATENT DOCUMENTS

| | | | |
|---|---|---|---|
| 5,443,152 A | 8/1995 | Davis | |
| 5,500,732 A | 3/1996 | Ebel | |
| 5,528,357 A | 6/1996 | Davis | |
| 5,568,715 A | 10/1996 | Ebel | |
| 5,578,331 A | 11/1996 | Martin | |
| 5,640,464 A | 6/1997 | Ebel | |
| 5,649,410 A | 7/1997 | Martin | |
| 5,675,962 A | 10/1997 | Martin | |
| 5,687,541 A | 11/1997 | Martin | |
| 5,719,668 A | 2/1998 | Oana | |
| 5,745,230 A | 4/1998 | Edwards | |
| 5,748,300 A | 5/1998 | Wilder | |
| 5,805,276 A | 9/1998 | Davis | |
| 5,812,254 A | 9/1998 | Ebel | |
| 5,828,446 A | 10/1998 | Davis | |
| 5,943,436 A | 8/1999 | Ebel | |
| 5,995,213 A | 11/1999 | Davis | |
| 6,154,274 A | 11/2000 | Davis | |
| 6,246,062 B1 | 6/2001 | Ross, III | |
| 6,577,387 B2 | 6/2003 | Ross, III | |
| 6,882,411 B2 | 4/2005 | Dispenza | |
| 7,990,531 B2 * | 8/2011 | Clements et al. | 356/239.2 |

FOREIGN PATENT DOCUMENTS

WO   WO 03073061 A2   9/2003

OTHER PUBLICATIONS

PCT International Search Report, dated Sep. 14, 2012, for PCT Int'l Appln. No. PCT/US2012/039995.
International Preliminary Report on Patentability, dated Dec. 4, 2013, for PCT Int'l. Appln. No. PCT/US2012/039995.

* cited by examiner

*Primary Examiner* — Tarifur Chowdhury
*Assistant Examiner* — Amanda Merlino
(74) *Attorney, Agent, or Firm* — Karen A. Harding

(57) ABSTRACT

Methods for inspecting ophthalmic lenses with different wavelengths of radiation are disclosed herein.

12 Claims, 2 Drawing Sheets

MULTIPLE RADIATION INSPECTION OF OPHTHALMIC LENSES

CROSS-REFERENCE TO RELATED APPLICATION

This application claims the benefit of U.S. Provisional Patent Application Ser. No. 61/492,932 filed Jun. 3, 2011.

FIELD OF THE INVENTION

This invention relates to the inspection of ophthalmic lenses, particularly silicone hydrogel contact lenses, using radiation of one or more wavelengths.

BACKGROUND OF THE INVENTION

Ophthalmic lenses, such as soft contact lenses are delivered to consumers in a single use package, (commonly referred to as a blister package) with an accompanying packaging solution. Typically such ophthalmic lenses are formed, inspected, and packaged on manufacturing lines with minimal human intervention.

Even with the aforementioned inspection methods, it is often difficult to distinguish between a defect, such as a hole in the ophthalmic lens and a bubble found in the solution. Such distinctions are critical because if lenses fail inspection due to the mischaracterization of defects, satisfactory products may be discarded in error and processes may be unnecessarily modified to account for defects to lenses that in fact do not exist. Therefore it is critical to be able to distinguish between defects in the ophthalmic lenses verses bubbles the packages. This need is met by the following invention.

DETAILED DESCRIPTION OF THE INVENTION

Figure 1:
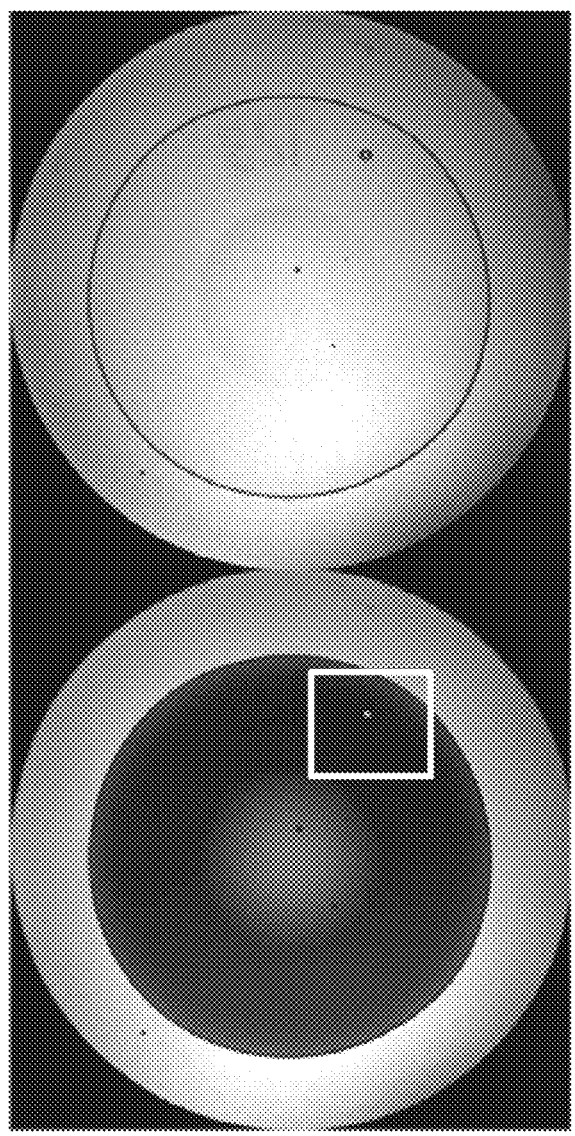
FIG. 1 Images of an ophthalmic lens with different wavelengths of light showing a hole.

This invention provides a method of inspecting a silicone hydrogel ophthalmic lens housed in a container with packaging solution that is moving through a manufacturing line comprising
  (a) illuminating the ophthalmic lens with radiation comprising one or more members of the group consisting of visible, ultraviolet, or infrared radiation to create a first image;
  (b) transferring the first image to an intermediate storage area
  (c) illuminating the ophthalmic lens with radiation comprising one or more members of the group consisting of visible, ultraviolet, or infrared radiation to generate a second image, provided that the illuminating radiation of step (c) is different from the illuminating radiation of step (a)
    wherein said illuminating of step (c) is conducted in a substantially short period of time after the illuminating of step (a)
  (d) transferring the first image from the intermediate storage area to an image capturing device
  (e) transferring the second image to the intermediate storage area
  (f) transferring the second image to the image capturing device
  (g) comparing the first image to the second image when viewed from the image capturing device to determine the ophthalmic lens contains defects.

As used herein the term "silicone hydrogel ophthalmic lens" refers to soft contact lenses made with monomers, macromers or prepolymers which contain silicone. Examples of such ophthalmic lenses include but are not limited to lenses made from the following generic formulations balafilcon, lotrafilcon, galyfilcon, enfilcon, comfilcon, senofilcon, and narafilcon. The preferred silicon hydrogel ophthalmic lens are made from the following formulations comfilcon, galyfilcon, senofilcon, and narafilcon. The particularly preferred ophthalmic lenses are made from the following formulations galyfilcon, senofilcon, and narafilcon.

As used herein, the term "container" means any receptacle which is used to house an ophthalmic lens and a solution either during the manufacturing process or thereafter. Examples of containers include but are not limited to trays, cups, lens molds, blister package bowls and the like. The preferred containers are trays and blister package bowls. At different points in the manufacturing process the ophthalmic lens may be in contact with a number of different aqueous and organic solutions. The preferred solutions for this method are aqueous solutions such as deionized water and saline solutions. The preferred solutions is deionized water.

The ophthalmic lenses are inspected as they move through different stations of an ophthalmic lens manufacturing line. The lens typically move at the speed of between about 1 and about 200 mm/second, preferably about 70 to about 120 mm/sec.

In the method, lenses are first illuminated with radiation comprising one or more members of the group consisting of visible, ultraviolet, or infrared radiation. Visible radiation has wavelengths from about 390 nm to about 700 nm, ultraviolet radiation has wavelengths from about 10 nm to about 390 nm, and infrared radiation has wavelengths from about 700 nm to about 3000 nm. It is preferred that the ophthalmic lens is illuminated in step (a) with radiation in the visible range, preferably radiation having a wavelength of about 440 nm to about 500 nm, more preferably about 440 nm to about 475 nm. It is preferred that the ophthalmic lens is illuminated in step (b) with radiation in the ultraviolet range, having a wavelength from about 300 nm to about 390 nm, more preferably, from about 370 nm to about 380 nm.

In addition, radiation for either step (a) or step (b) may comprise a combination of two or more types of radiation such as ultraviolet, visible and infrared radiation. Techniques for determining the proportion of such each type of radiation are disclosed in U.S. Pat. No. 6,882,411 which is hereby incorporated by reference in its entirety. It is preferred that step (a) comprises visible and ultraviolet radiation.

The radiation may be supplied by two radiation sources, which supply different wavelengths, or by a single source which produces multiple wavelengths of light. Such radiation sources provide either continuous radiation, or pulsed radiation, where the spacing between the pulses is coordinated with the timing of image production.

As used herein "intermediate storage area" means an interline shift register found within the interline transfer architecture of a CCD chip. Such intermediate storage areas allow two successive images to be captured with a substantially short period of time. The intermediate storage area is located inside of a camera. In addition to the intermediate storage area, the preferred cameras used in the methods of the invention contain special optics to minimize the focus shifts caused by capturing images using radiation of different spectral bands. Cameras which can be used in the invention include but are not limited to cameras such as the Dalsa 4M15 Pantera, RMV-4021 Illunis. The preferred cameras have sensors which are sealed within the camera housing to minimize contamination to the sensor which can cause false artifacts to appear in images. The imaging optic design also avoids creating intermediate image planes within the camera lens' optical chain that are close to lens element surfaces to prevent contamination within the camera lens housing from appearing as false artifacts in the images. The preferred cameras used in the methods of the invention have a field of view of about 14 mm to about 22 mm, more preferably about 17 mm.

As used herein, "substantially short period of time" is the time between the illumination and image capture of step (a) and the illumination and image capture of step (c). This substantially short period of time is preferably between 1 microsecond and 500 microseconds, more preferably between about 75 microseconds to about 200 microseconds. This period of time permits the camera to capture the entire image of the ophthalmic lens in both the first image and the second image before the lens moves beyond the field of view of the camera As used herein, "image analysis device" means any instrument capable of storing and optionally subsequently manipulating an image. Examples of such image analysis devices include but are not limited to computers with associated software, cameras such as GigE, IEEE 1394 camera, and other cameras connected to computers via USB. The preferred image analysis device is a computer which contains various algorithms to analyze the stored images and a frame grabber. In one embodiment of the invention, the software of the image analysis device analyzes each image independently prior to comparing the images, this is the preferred method of analyzing the images. In another embodiment, the software combines both images and analyzes them at the same time.

This method may be combined with other techniques for inspecting ophthalmic lenses. Non-limiting examples of such techniques are disclosed in the following U.S. Pat. Nos. 6,882,411, 6,577,387, 6,246,062; 6,154,274; 5,995,213; 5,943,436; 5,828,446; 5,812,254; 5,805,276; 5,748,300; 5,745,230; 5,687,541; 5,675,962; 5,649,410; 5,640,464; 5,578,331; 5,568,715; 5,443,152; 5,528,357; and 5,500,732; all of which are incorporated herein in their entireties by reference.

EXAMPLE

Images of a silicone hydrogel lens are produced using the methods of the invention as follows. Lenses moving at a rate of 100 mm/sec, are illuminated with visible light having a wavelength of 465 nm. This captured image is transferred to a frame grabber and displayed as seen in the top half of FIG. 1. The second image in the bottom half of FIG. 1 was illuminated with ultraviolet light having a wavelength of 375 nm, 200 microseconds after the first image, captured and transferred to the frame grabber. FIG. 1 shows that the area within the square box is a hole because the image of the lower half shows a relatively bright spot within the square compared to its surroundings and thus confirms that material is missing.

Figure 2:
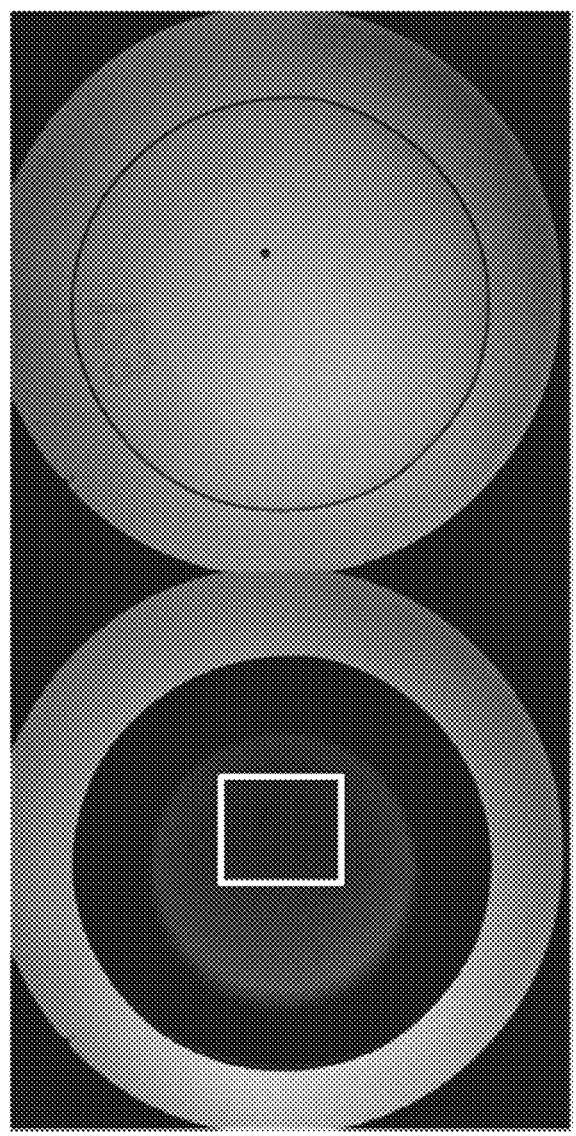
FIG. 2 Images of an ophthalmic lens with different wavelengths of light showing a bubble.

The same procedure was to obtain the upper and lower images of FIG. 2. These images confirm that the area in the square is a bubble because it is not bright within the square compared to its surroundings and thus the lower image does not show missing material.

We claim:

1. A method of inspecting a silicone hydrogel ophthalmic lens housed in a container with packaging solution that is moving through a manufacturing line comprising
    (a) illuminating the ophthalmic lens with radiation comprising one or more members of the group consisting of visible, ultraviolet, or infrared radiation to create a first image;
    (b) transferring the first image to an intermediate storage area
    (c) illuminating the ophthalmic lens with radiation comprising one or more members of the group consisting of visible, ultraviolet, or infrared radiation to generate a second image, provided that the illuminating radiation of step (c) is different from the illuminating radiation of step (a)
        wherein said illuminating of step (c) is conducted in a substantially short period of time after the illuminating of step (a)
    (d) transferring the first image from the intermediate storage area to an image capturing device
    (e) transferring the second image to the intermediate storage area
    (f) transferring the second image to the image capturing device
    (g) comparing the first image to the second image when viewed from the image capturing device to determine if the ophthalmic lens contains defects.

2. The method of claim 1 wherein the ophthalmic lens is illuminated with visible radiation in step (a).

3. The method of claim 1 wherein the ophthalmic lens is illuminated in step (a) with radiation having a wavelength of about 400 nm to about 500 nm.

4. The method of claim 1 wherein the ophthalmic lens is illuminated in step (a) with radiation having a wavelength of about 465 nm.

5. The method of claim 1 wherein the ophthalmic lens is illuminated in step (c) with radiation having a wavelength of about 365 to about 385 nm.

6. The method of claim 1 wherein the ophthalmic lens is illuminated in step (c) with radiation having a wavelength of about 375.

7. The method of claim 1 wherein the substantially short period of time is about 1 microsecond to 300 microseconds.

8. The method of claim 1 wherein the intermediate storage area is an interline shift register within an interline transfer architecture of a CCD chip.

9. The method of claim 1 wherein the speed of the manufacturing line is about 200 mm/sec.

10. The method of claim 1 wherein the ophthalmic lens is illuminated with ultraviolet radiation in step (a).

11. The method of claim 1 wherein the ophthalmic lenses are illuminated by pulses of radiation of different wavelengths.

12. The method of claim 11 wherein the pulses of radiation of different wavelengths occurs at different times where the time in between is a substantially short period of time.

* * * * *